United States Patent [19]

Pearson et al.

[11] Patent Number: 4,685,958
[45] Date of Patent: Aug. 11, 1987

[54] SULFONAMIDES DERIVED FROM SUBSTITUTED 2-AMINO-1,2,4-TRIAZOLO[1,5-A]-1,3,5-TRIAZINES AND COMPOSITIONS AND METHODS OF CONTROLLING UNDESIRED VEGETATION

[75] Inventors: Norman R. Pearson, Walnut Creek; William A. Kleschick, Martinez, both of Calif.

[73] Assignee: The Dow Chemical Company, Midland, Mich.

[21] Appl. No.: 860,160

[22] Filed: May 6, 1986

[51] Int. Cl.$^4$ .................... C07D 487/04; A01N 43/90
[52] U.S. Cl. ........................................ 71/93; 544/211; 544/212; 544/206; 544/207; 544/208; 544/209

[58] Field of Search ................... 71/93; 544/211, 212, 544/206, 207, 208, 209

[56] References Cited

U.S. PATENT DOCUMENTS 3,910,907 10/1975 O'Brien et al. ...................... 544/212
4,565,815 1/1986 Kim et al. ........................... 544/212
4,605,433 8/1986 Pearson et al. ........................ 71/93

Primary Examiner—John M. Ford
Attorney, Agent, or Firm—Merlin B. Davey

[57] ABSTRACT

Novel compounds, e.g., N-(5,7-dimethyl-1,2,4-triazolo[1,5-a]-1,3,5-triazin-2-yl)-(2-chlorobenzenesulfonamide) and their compositions and use in the control of weeds.

11 Claims, No Drawings

SULFONAMIDES DERIVED FROM SUBSTITUTED 2-AMINO-1,2,4-TRIAZOLO[1,5-A]-1,3,5-TRIAZINES AND COMPOSITIONS AND METHODS OF CONTROLLING UNDESIRED VEGETATION

BACKGROUND OF THE INVENTION

In recent years there has been a great deal of effort directed to the development of sulfonamides having herbicidal activity and several of these compounds have reached the stage of commercialization, i.e., chlorsulfuron and sulfometuron methyl. These compounds exhibit both preemergence and postemergence activity against undesirable vegetation and, in addition, have a low toxicity to mammals. The compounds of the prior art may be depicted as follows:

wherein Ar is usually a benzene derivative and Ar' is usually a pyrimidine or symmetrical triazine derivative.

In addition, there are a number of other sulfonamide herbicides that have been commercialized, for example, methyl sulfanilylcarbamate; O,O-diisopropyl phosphorodithioate-S-ester with N-(2-mercaptoethyl)-benzenesulfonamide; 3-isopropyl-1H-2,1,3-benzothiadiazin-4(3H)-one 2,2-dioxide; N-[2,4-dimethyl-5-[[(trifluoromethyl)sulfonyl]amino]phenyl]acetamide; and 3,5-dinitro-$N^4$,$N^4$-dipropylsulfanilamide.

SUMMARY OF THE INVENTION

I have now found that compounds having the formula:

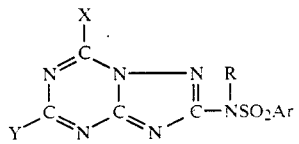

wherein R represents hydrogen, alkyl, alkenyl, alkynyl, phenylalkyl, substituted phenylalkyl, acyl, alkoxycarbonyl, phenyloxycarbonyl, dialkylaminocarbonyl, alkylsulfonyl, phenylsulfonyl, alkylthiocarbonyl or phenylthiocarbonyl, each containing one to ten carbon atoms, Ar represents a substituted or unsubstituted mono or bicyclic aromatic or heteroaromatic (containing one or more or a combination of N, O or S atoms) ring system containing five or six-membered rings, where the substituents are halo, alkyl, haloalkyl, phenyl, hydroxy, alkoxy, haloalkoxy, phenoxy, amino, alkylamino, dialkylamino, nitro, alkylthio, haloalkylthio, alkylsulfinyl, haloalkylsulfinyl, alkylsulfonyl, haloalkylsulfonyl, phenylthio, phenylsulfinyl, phenylsulfonyl, cyano, carboxylic acids, carboxylate esters, sulfonic acids, sulfonate esters, sulfonamides, formyl, alkylcarbonyl, haloalkylcarbonyl, or phenylcarbonyl, are active herbicides and are readily produced.

DETAILED DESCRIPTION OF THE INVENTION

The aromatic or heteroaromatic ring systems include, for example, phenyl; 1- or 2-napthyl; 2-, 3- or 4-pyridyl; 2- or 3-thienyl; 2- or 3-furyl; 2-, 4- or 5-thiazolyl; 2-, 4- or 5-imidazolyl; 2-, 4- or 5-oxazolyl; 3-, 4- or 5-isothiazolyl; 3-, 4- or 5-isoxazolyl; 3-, 4- or 5-pyrazolyl; 2-benzthiazolyl; 2-benzoxazolyl; 2-benzimidiazolyl and 1-benztriazolyl. Typical examples of substituents found on the aromatic or heteroaromatic ring systems may be one, more than one or a combination of the following: halo (F, Cl, Br, I), $C_1$–$C_6$ alkyl, $C_1$–$C_6$ haloalkyl, phenyl, hydroxy, $C_1$–$C_6$ alkoxy, $C_1$–$C_6$ haloalkoxy, phenoxy, substituted phenoxy, heteroaryloxy, substituted heteroaryloxy, amino, $C_1$–$C_6$ alkylamino, $C_1$–$C_6$ dialkylamino, nitro, $C_1$–$C_6$ alkylthio, $C_1$–$C_6$ haloalkylthio, $C_1$–$C_6$ alkylsulfinyl, $C_1$–$C_6$ haloalkylsulfinyl, $C_1$–$C_6$ alkylsulfonyl, $C_1$–$C_6$ haloalkylsulfonyl, substituted or unsubstituted phenylthio, substituted or unsubstituted phenylsulfinyl, substituted or unsubstituted phenylsulfonyl, cyano, carboxylic acids (and derivatives of carboxylic acids such as esters derived from readily available alcohols and amides derived from ammonia or readily available primary and secondary amines), sulfonic acids (and derivatives of sulfonic acids such as sulfonates derived from readily available alcohols and sulfonamides derived from ammonia or readily available primary or secondary amines), formyl, $C_1$–$C_6$ alkylcarbonyl, $C_1$–$C_6$ haloalkylcarbonyl, phenylcarbonyl, substituted phenylcarbonyl, oximino, oxime ethers, carbinols (and carbinol derivatives such as ethers and esters derived from readily available alkylating agents and carboxylic acids respectively) and $C_1$–$C_6$ mercaptoalkyl (and derivatives of mercaptoalkyl groups such as thioethers and thioesters derived from readily available alkylating agents and carboxylic acids respectively).

The substituents on the triazolopyrimidine fragment of structure I are represented by X and Y. Substituents X and Y may be H, $C_1$–$C_6$ alkyl, $C_1$–$C_6$ haloalkyl, hydroxy, $C_1$–$C_6$ alkoxy, $C_1$–$C_6$ haloalkoxy, phenyl, substituted phenyl, halo (F, Cl, Br, I), $C_1$–$C_6$ alkylthio, phenylthio, amino (including alkyl and phenyl substituted amino), carboxylic acids and esters.

Preferred compounds of the invention have the general formula:

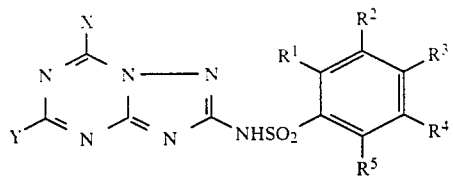

Wherein $R^1$ represents halo (F, Cl, Br, I), —$NO_2$, phenyl, OAr, —$CF_3$, —$OCF_3$, —$OCF_2CF_2H$, —$OCF_2CCl_2H$, —$OCH_2CF_3$, —$SCF_3$, —$SCF_2CF_2H$, —$SCF_2CCl_2H$, —$SOCF_3$, —$SOCF_2CF_2H$, —$SOCF_2CCl_2H$, —$SO_2CF_3$, —$SO_2CF_2CF_2H$, —$SO_2CF_2CCl_2H$, —$SR^6$, —$SOR^6$, —$SO_2R^6$, —CN, —$COOR^7$, —$CONH_2$, —$CONHR^8$, —$CONR^8(R^9)$, —$SO_3R^8$ and —$SO_3CH_2CF_3$; $R^2$ and $R^4$ represent H, halo (F, Cl, Br, I), $C_1$–$C_4$ alkyl, $COOR^7$ and —$OR^8$; $R^3$ is H; and $R^5$ represents H, $C_1$ to $C_4$ alkyl, halo (F, Cl, Br, I), $NO_2$, $CF_3$, —$OCF_3$, —$OCF_2CF_2H$, —$OCF_2CCl_2H$, —$OCH_2CF_3$, —$SCF_3$, —$SCF_2CF_2H$, —$SCF_2CCl_2H$, —$SOCF_3$, —$SOCF_2CF_2H$, —$SOCF_2CCl_2H$, —$SO_2CF_3$, —$SO_2CF_2CF_2H$, —$SO_2CF_2CCl_2H$, —$SR^6$, —$SOR^6$, —$SO_2R^6$, —CN, —$COOR^7$, —$CONH_2$, $CONHR^8$, —$CONR^8(R^9)$, —$SO_3R^8$, —$SO_3CH_2CF_3$, —$CR^6R^6OR^6$ and —$CR^6R^6SR^6$ wherein Ar represents substituted or unsubstituted phenyl or substituted or unsubstituted heteroaryl (e.g., 2-pyridyl), $R^6$ represents H, phenyl or $C_1-C_4$ alkyl, $R^7$ represents $C_1-C_6$ alkyl, alkenyl, alkynyl, aryl, substituted alkyl or substituted phenyl and $R^8$ and $R^9$ individually represent $C_1-C_4$ alkyl; and X and Y represent H, $C_1-C_4$ alkyl, $C_1-C_4$ alkoxy, $C_1-C_4$ haloalkyl, $C_1-C_4$ haloalkoxy, $C_1-C_4$ alkylthio, or halo (F, Cl, Br, I).

Preferred compounds of the invention also have the general formula:

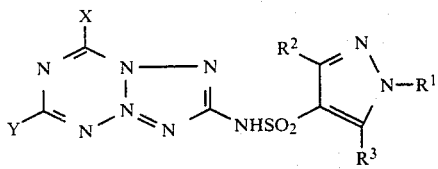

wherein $R^1$ represents H, $C_1-C_4$ alkyl or phenyl, $R^2$ and $R^3$ represent independently H, $C_1-C_4$ alkyl, halo (F, Cl, Br, I), —$NO_2$, phenyl, —$CF_3$, benzyl, —$COOR^4$, —$CONH_2$, —$CONHR^5$, —$CONR^5R^6$, and CN wherein $R^4$ represents $C_1-C_6$ alkyl, alkenyl, alkynyl, phenylalkyl, substituted alkyl or substituted phenyl, $R^5$ and $R^6$ individually represent $C_1-C_4$ alkyl; and X and Y represent H, $C_1-C_4$ alkyl, $C_1-C_4$ alkoxy, halo (F, Cl, Br, I).

In addition certain derivatives of compounds corresponding to I also exhibit herbicidal activity. For example, compounds having the formula:

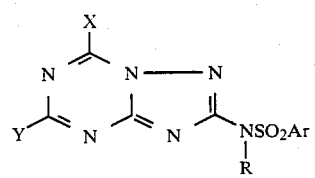
(II)

wherein Ar and X and Y are as described above for compound I and R represents alkyl, alkenyl, alkynyl, phenylalkyl, substituted phenylalkyl, acyl, alkoxycarbonyl, phenoxycarbonyl, dialkylaminocarbonyl, alkylsulfonyl, phenylsulfonyl, alkylthiocarbonyl or phenylthiocarbonyl, each containing from one to ten carbon atoms.

Preferred derivatives of the invention have the general formula:

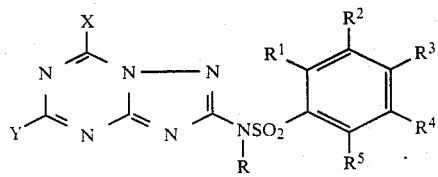

wherein X, Y, $R^1$, $R^2$, $R^3$, $R^4$ and $R^5$ are as described above and R represents $C_1-C_4$ alkyl, allyl, benzyl, —$COR^{10}$, —$CO_2R^{10}$, —$CONR_2^{10}$, —$COSR^{10}$, and —$SO_2R^{10}$ wherein $R^{10}$ is $C_1-C_6$ alkyl, phenyl, substituted phenyl or haloalkyl.

The synthesis of compounds of general structure I can be carried out in a straightforward manner as illustrated in Scheme I. Reaction of the appropriate aromatic sulfonyl chloride IV with the required 2-amino-1,2,4-triazolo[1,5-a]-1,3,5-triazine V under basic conditions yields the desired product I. A wide range of solvents may be employed (i.e., $CH_2Cl_2$, $CH_3CN$ or pyridine) at temperatures ranging from 0° C. to reflux. Bases which serve as catalysts include pyridine, 4-dimethylaminopyridine and teritary alkylamines such as triethylamine or N-methylmorpholine. Generally the amino compound V serves as the limiting reagent. Molar ratios of between 1.1 and 1.0 for the sulfonylchloride to amino compound and molar ratios of between 5.0 and 1.1 for the base to amino compound are used most often. A wide range of concentrations may be employed (i.e., 0.1-5M). In addition it is sometimes advantageous to use a combination of pyridine derived base catalysts and tertiary amine bases. The use of pyridine as a solvent is convenient as the pyridine can serve both as a solvent and catalyst in the transformation.

SCHEME I

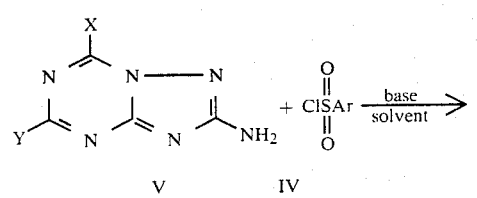

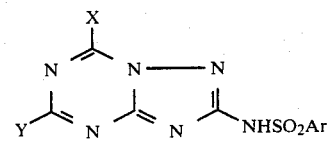

I

The required sulfonyl chlorides IV are often commercially available. In some cases sulfonyl chlorides are prepared by the methodology outlined by H. T. Clarke et al., *Org. Synth.* Coll., Vol. 1, 2nd Ed., 1941, p. 85. This involves chlorosulfonation of the appropriate substituted benzene. Other sulfonyl chlorides can be prepared by methods described by R. V. Hoffman, *Org. Synth.*, Vol. 60, p. 121. This involves diazotization of the appropriate substituted aniline or amino substituted heterocycle with sodium nitrite in acidic media followed by reaction of the diazonium salt with sulfur dioxide in the presence of cuprous chloride. In addition certain sulfonyl chlorides can be prepared from aromatic compounds containing mercapto or benzylthio groups. The mercapto or benzylthio functional group is converted to a sulfonyl chloride by treatment with chlorine in aqueous acidic media.

The required substituted 2-amino-1,2,4-triazolo[1,5-a]-1,3,5-triazine V can be prepared as illustrated in Scheme II. The triazine ring may

SCHEME II

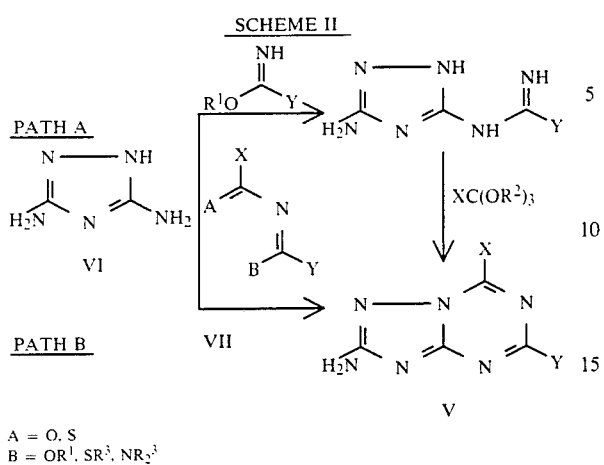

A = O, S
B = OR¹, SR³, NR₂³ be constructed in two steps (PATH A) by treatment of 3,5-diamino-1,2,4-triazole VI with an imidate ester followed by an orthoester, or in one step (PATH B) using reagents of structure VII. Analogous procedures have been described in the literature for preparing fused triazines starting with 3-aminopyrazoles (J. Het. Chem., 12, 1255 (1975) and J. Het. Chem., 22, 7 (1985)).

Compounds of the present invention represented by structure II are derived from compounds represented by structure I as illustrated in Scheme III. The derivatization procedure involves treatment of compound I with a base in a suitable solvent followed by the introduction of an appropriate electrophilic derivatizing reagent. From this process compounds of general structure II can be isolated in good yields. Suitable bases include tertiary alkylamines (i.e., triethylamine), pyridine, 4-dimethylaminopyridine, alkali metal carbonate (i.e., Na₂CO₃ or K₂CO₃) and alkali metal alkoxides (i.e., sodium ethoxide or potassium t-butoxide). Suitable solvents include ethers (i.e., tetrahydrofuran), pyridine, acetone, acetonitrile, alcohols (i.e., methanol, ethanol, isopropanol and t-butanol) and polar aprotic solvents (i.e., DMSO and DMF). Suitable electrophilic reagents include alkyl halides, arylalkyl halides (i.e., benzyl chloride), carboxylic acid chlorides, alkyl chloro formates, aryl chloro formates, N,N-dialkyl carbamoyl chlorides, alkyl sulfonyl chlorides, aryl sulfonyl chlorides, alkyl chloro thioformates

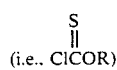
(i.e., ClCOR)

and aryl chlorothioformates

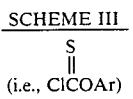
(i.e., ClCOAr)

SCHEME III

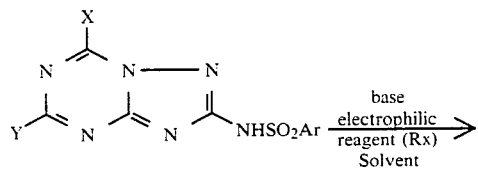

-continued
SCHEME III

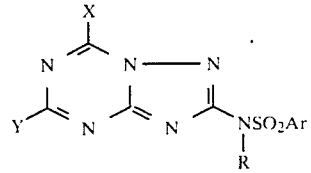

A further procedure for the preparation of compounds of Formula I is illustrated in Scheme IV. In accordance with this process the sulfonamides VIII are reacted with dimethyl N-cyanodithioiminocarbonate in the presence of a base in a solvent. Bases which are effective in this transformation include tertiary amines (i.e. triethylamine) or alkali metal hydroxides, alkoxides or carbonates (i.e. NaOH, NaOCH₃ or K₂CO₃). Appropriate solvents include acetone, methyl ethyl ketone, acetonitrile or tetrahydrofuran (THF). The reaction may be run at temperatures ranging from ambient temperature to reflux. The products of this transformation IX may be isolated directly as their salts and converted to their neutral species by acidification. In some instances the salt may be used directly in subsequent transformations without isolation, purification or conversion to the corresponding neutral species. Compound IX may be reacted with an excess of hydrazine to form the intermediate 1,2,4-triazoles X. This reaction is generally carried out in solvents such as acetonitrile, THF, DMF, or DMSO at ambient temperature although higher temperatures may be employed to increase the rate of reaction. The amount of excess hydrazine utilized in this transformation ranges from 5 to 400 mole percent. The final step in this sequence for the conversion of compound X to I may be carried out as illustrated in Scheme II.

Scheme IV

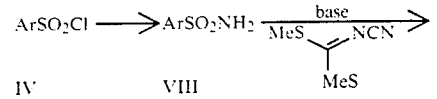

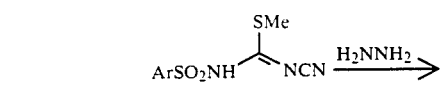

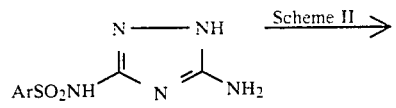

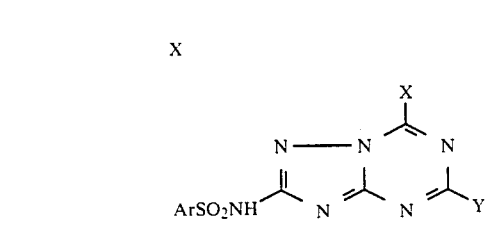

An alternative procedure for the synthesis of intermediates of general structure IX is illustrated in the following equation. The starting materials XI may be prepared from aromatic sulfonamides by known art (i.e. F. L. Merchan, *Synthesis*, 984 (1982); R. Gompper, et al., *Chem. Ber.*, 99, 2885, 2990 (1966)). These intermediates may be reacted with cyanamide in the presence of base to form IX. Bases include tertiary amines and alkali metal alkoxides, hydroxides and carbonates. This reaction is most frequently carried out in acetonitrile or THF at temperatures ranging from ambient temperature to reflux.

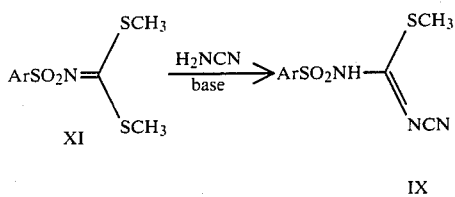

In certain instances intermediates XI may be converted to their corresponding mono or dichloro derivatives (i.e. XII and XIII respectively). This may be accomplished by known art (i.e. E. Kuhle, et al., *Angew, Chem Int. Ed. Engl.*, 6, 649 (1967)). These intermediates may then be advantageously used in a manner analogous to XI in the synthesis of compounds of general structure I.

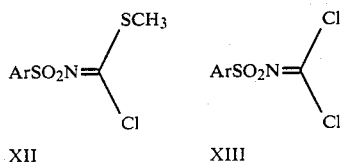

Using the routes illustrated above or minor variations based on the principles illustrated above the novel compounds of this invention can be prepared.

The invention is further illustrated by the following examples.

EXAMPLE 1

N'-Cyano-N-(2-nitrophenylsulfonyl)-2-methylisothiourea.

A mixture of 2.02 g (10.0 mmol) of 2-nitrobenzenesulfonamide, 1.46 g (10.0 mmol) of dimethyl N-cyanodithioiminocarbonate and 1.38 g (10.0 mmol) of powdered, anydrous $K_2CO_3$ in 16 ml of acetone was heated at reflux for 20 hours. The reaction mixture was filtered and the solid collected was washed several times with acetone. The filtrate was evaporated and the orange oily residue was triturated with ether to afford a solid. The solid was collected by filtration, washed with ether and suspended in 10 ml of 1N HCl. After stirring for 1 hour the solid was collected by filtration, washed with water and dried to yield 1.65 g (55 percent) of the desired product as a cream colored solid, mp 122° C. (decomposition). IR and $^1$H NMR spectra were consistent with the assigned structure.

Analysis: Calculated for $C_9H_8N_4O_4S_2$: C, 36.00; H, 2.69; N, 18.66; S, 21.35. Found: C, 36.10; H, 2.74; N, 18.72; S, 21.22.

EXAMPLE 2

N-(5-Amino-1,2,4-triazol-3-yl)-2-nitrobenzenesulfonamide

A suspension of 29.4 g (98.0 mmol) of N'-Cyano-N-(2-nitrophenylsulfonyl)-S-methylisothiourea in 100 ml of acetonitrile was treated with 6.2 ml (6.3 g, 0.20 mol) of anhydrous hydrazine. A mild exothermic reaction occurred as the reaction mixture became homogeneous. After stirring for 9 days the precipitated solid was collected by filtration and dried to afford 22.9 g of yellow solid. The crude product was recrystallized from HOAc to yield a total of 15.9 g (57 percent) of the desired product as a pale yellow solid, mp 255°–256° C. IR and $^1$H NMR spectra were consistent with the assigned structure.

Analysis: Calculated for $C_8H_8N_6O_4S$: C, 33.80; H, 2.84; N, 29.57; S, 11.28. Found: C, 34.11; H, 2.79; N, 29.35; S, 11.50.

EXAMPLE 3

N'-Cyano-N-(2,5-dichlorophenylsulfonyl)-S-methylisothiourea

A solution of 10.6 g (43.2 mmol) of 2,5-dichlorobenzenesulfonamide, 7.15 g (44.0 mmol) of 90 percent dimethyl N-cyanodithioiminocarbonate and 1.8 g (44 mmol) of NaOH in 60 ml of ethanol and 10 ml of $H_2O$ was heated at reflux for 6 hours. After cooling to room temperature the reaction mixture was poured into 600 ml of ice water. The resulting solution was acidified with 6N HCl to separate 2.2 g of the desired product as a white solid. Concentration of the filtrate gave an additional 8.5 g of the desired product. The total yield of material was 10.7 g (76 percent) of white solid, mp 145° C. IR and $^b$ $^1$H NMR spectra were consistent with the assigned structure.

Analysis: Calculated for $C_9H_7Cl_2N_3O_2S_2$: C, 33.34; H, 2.18; N, 12.96. Found: C, 33.50; H, 2.39; N, 12.82.

EXAMPLE 4

N-(5-Amino-1,2,4-triazol-3-yl)-2,5-dichlorobenzenesulfonamide

A mixture of 8.51 g (26.2 mmol) of N'-cyano-N-(2,5-dichlorophenylsulfonyl)-S-methylisothiourea and 10 ml (10 g, 0.20 mol) of hydrazine monohydrate in 85 ml of ethanol was heated at reflux for 30 minutes. After cooling to room temperature, the solid which separated was collected and suspended in 170 ml of $H_2O$ and the suspension was acidified with concentrated aqueous HCl. After stirring the suspension for 4 hours the solid was collected and dried in vacuo to yield 5.10 g (57 percent) of the desired product as a hydrochloride salt, mp 306°–308° C. IR and $^1$H NMR spectra were consistent with the assigned structure.

Analysis: Calculated for $C_8H_7Cl_2N_5O_2S \cdot HCl$: C, 27.88; H, 2.34; N, 20.32. Found: C, 28.36; H, 2.50; N, 19.78.

EXAMPLE 5

N-(5,7-Dimethyl-1,2,4-triazolo[1,5-a]-1,3,5-triazin-2-yl)-(2-chlorobenzene)-sulfonamide A solution of 2.00 gm (7.31 mmol) of N-(5-amino-1,2,4-triazol-3-yl)-2-chlorobenzenesulfonamide in 20 mL of DMF was treated with 1.04 gm (8.04 mmol) of ethyl N-acetylacetimidate and the resulting solution stirred at 60°–65° C. for 20 hours. The solution was then treated with an additional 0.24 gm (1.9 mmol) of the starting imidate ester, stirred at 65°–70° C. for another 20 hours and then concentrated in vacuo (xylene chaser) to afford 2.50 gm of a yellow solid. This material was then triturated with 50 ml of boiling acetonitrile, cooled to room temperature, and filtered. The filtrate was concentrated in vacuo and the solid obtained again subjected to trituration with hot acetonitrile, cooling, filtration, concentration of the filtrate in vacuo, and drying in vacuo, to provide 1.30 gm (53%) of a pale, yellow solid, m.p. 189°–193° C. IR and $^1$H NMR spectra were consistent with the assigned structure.

Analysis: Calculated for $C_{12}H_{11}ClN_6O_2S$: C, 42.55; H, 3.27; N, 24.80. Found: C, 42.58; H, 3.43; N, 24.97.

EXAMPLE 6

Ethyl N-acetylacetimidate

A slurry of 50.0 gm (405 mmol) of ethyl acetimidate hydrochloride in 500 ml of methylene chloride was mechanically stirred and treated dropwise with 81.9 gm (809 mmol) of triethylamine while keeping the temperature at less than 25° C. The resulting slurry was then treated dropwise with 31.8 gm (405 mmol) of acetyl chloride while keeping the temperature at less than 30° C. The white slurry was stirred for one hour at room temperature, after which the methylene chloride was removed in vacuo. The white, oily mass obtained was then stirred with 400 ml of ether and filtered. The white solid obtained was washed with additional ether and the combined filtrate was concentrated in vacuo to afford 48.6 gm (93 percent) of a pale, yellow oil. IR and NMR spectra were consistent with the assigned structure.

Exact mass: Calculated for $C_6H_{11}NO_2$:129.0790. Found: 129.0788.

The compounds of the present invention are highly effective herbicides. They have utility for broadspectrum pre- and/or postemergence weed control in areas where complete vegetation control is desired. The subject compounds are also useful for selective pre- and/or postemergence weed control in crops such as wheat. Certain of these compounds are effective for the control of nutsedge (Cyperus spp.) and some compounds may be used for selective weed control in corn, soybeans and rice.

For all such uses, unmodified active ingredients of the present invention can be employed. However, the present invention embraces the use of a herbicidally-effective amount of the active ingredients in composition form with an inert material known in the art as an agricultural adjuvant or carrier in solid or liquid form. Such adjuvants or carriers must not be phytotoxic to valuable crops particularly at the concentration employed in applying the composition in attempting selective weed control in the presence of crops. If weed control is desired in the absence of crops, it is generally sufficient to employ adjuvants or carriers which do not leave a persistent phytotoxic residue.

Thus, for example, an active ingredient can be dispersed on a finely-divided solid and employed therein as a dust. Also, the active ingredients, as liquid concentrates or solid compositions comprising one or more of the active ingredients can be dispersed in water, typically with aid of a wetting agent, and the resulting aqueous dispersion employed as a spray. In other procedures the active ingredients can be employed as a constituent of organic liquid compositions, oil-in-water and water-in-oil emulsions or dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

Organic solvents that can be employed include toluene, xylene, kerosene, diesel fuel, fuel oil, and petroleum naphtha, ketones such as acetone, methylethyl ketone and cyclohexanone, chlorinated hydrocarbons such as trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butylcarbitol acetate and glycerine. Mixtures of water and organic solvents, either as emulsions or solutions, can be employed.

The active ingredients of the present invention can also be applied as aerosols, e.g., by dispersing them by means of a compressed gas such as one of the fluorocarbons or one of its hydrocarbon successors.

The active ingredients of the present invention can also be applied with solid adjuvants or carriers such as talc, pyrophyllite, synthetic fine silica, attapulgus clay, kieselguhr, chalk, diatomaceous earth, lime, calcium carbonate, bentonite, Fuller's earth, cotton seed hulls, wheat flour, soybean flour, pumice, tripoli, wood flour, walnut shell flour, redwood flour and lignin.

As stated, it is frequently desirable to incorporate a surface-active agent in the compositions of the present invention. Such surface-active or wetting agents are advantageously employed in both the solid and liquid compositions. The surface-active agent can be anionic, cationic or nonionic in character.

Typical classes of surface-active agents include alkyl sulfonate salts, alkylaryl sulfonate salts, alkylaryl polyether alcohols, fatty acid esters of polyhydric alcohols and the alkylene oxide addition products of such esters, and addition products of long-chain mercaptans and alkylene oxides. Typical examples of such surface-active agents include the sodium alkylbenzene sulfonates having 10 to 18 carbon atoms in the alkyl group, alkyl phenol ethylene oxide condensation products, e.g., p-isooctylphenol condensed with 20 ethylene oxide units, soaps, e.g., sodium stearate and potassium oleate, sodium salt of propylnaphthalene sulfonic acid, di(2-ethylhexyl)ester of sodium sulfosuccinic acid, sodium lauryl sulfate, sodium decyl sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, sodium dibutylnaphthalene sulfonate, sodium lignin sulfonate, polyethylene glycol stearate, sodium dodecyl benzene sulfonate, tertiary dodecyl polyethylene glycol thioether (nonionic 218), long-chain ethylene oxide-propylene oxide condensation products e.g., Pluronic 61 (molecular weight about 1000), polyethylene glycol ester of tall oil acids, sodium octophenoxyethoxyethyl sulfate, tris(polyoxyethylene)-sorbitan monostearate (Tween 60), and sodium dihexylsulfosuccinate.

Other adjuvants, such as, for example, crop oil and crop oil concentrates, may also be included in the formulated compositions of the invention as is known to those skilled in the art.

The herbicidally effective concentration of the active ingredients in solid or liquid compositions generally is from about 0.0003 to about 95 percent by weight or more. concentrations from about 0.05 to about 50 percent by weight are often employed. In compositions to be employed as concentrates, the active ingredient can be present in a concentration from about 5 to about 98 weight percent, preferably 15–50 weight percent. The active ingredient compositions can also contain other compatible additaments, for example, phytotoxicants, plant growth regulants, pesticides and the like and can be formulated with solid particulate fertilizer carriers such as ammonium nitrate, urea and the like.

In further embodiments, the compounds of the present invention or compositions containing the same, can be advantageously employed in combination with one or more additional pesticidal compounds. Such additional pesticidal compounds may be insecticides, nematocides, miticides, arthropodicides, herbicides, fungicides or bactericides that are compatible with the compounds of the present invention in the medium selected for application. In such embodiments, the pesticidal compound is employed as a supplemental toxicant for the same or for a different pesticidal use or as an additament.

The compounds of the present invention are particularly useful in combination with other herbicides including the substituted urea herbicides such as 3-(3,4-dichlorophenyl)-1,1-dimethylurea, 3-(3,4-dichlorophenyl)-1-methoxy-1-methylurea (Lorox ®) and 1,1-dimethyl-3-(α,α,α-trifluoro-m-tolyl)urea (Cotoran ®); the triazines such as 2-chloro-4-(ethylamino)-6-(isopropylamino)-s-triazine and 2-chloro-4-(1-cyano-1-methylethylamino)-6-ethyl-amino-s-triazine (Bladex ®); the uracils such as 5-bromo-3-sec-butyl-6-methyluracil; N-(phosphonomethyl)glycine; the phenoxys such as 2,4-dichlorophenoxyacetic acid; picolinic acids such as 4-amino-3,5,6-trichloropicolinic acid (Tordon ®) and 3,6-dichloropicolinic acid (Lontrel ®); 4-chloro-2-butynyl-3-chlorophenyl carbamate (Carbyne ®); diisopropylthiocarbamic acid, ester with 2,3-dichloroallyl alcohol (Avadex ®); diisopropylthiocarbamic acid, ester with 2,3,3-trichloroallyl alcohol (Avadex ® BVD); ethyl-N-benzoyl-N-(3,4-dichlorophenyl)-2-aminopropionate (Suffix ®); 1,2-dimethyl-3,5-diphenylpyrazolium methylsulfate (Avenge ®); methyl (2-[4-(2,4-dichlorophenoxy)-phenoxy]propanoate) (Hoelon ®); butyl 2-[4-[(5-(trifluoromethyl)-2-pyridinyl)oxy]phenoxy]propanoate (Fusilade ®); esters of 2-[4-[(3-chloro-5-trifluoromethyl)-2-pyridinyl)oxy]phenoxy]propionic acid; 4-amino-6-tert-butyl-3-(methylthio)-1,2,4-triazin-5-(4H)-one (Lexone ®); 3-isopropyl-1H-2,1,3-benzothiadiazin-(4)-3H-one 2,2-dioxide; α,α,α-trifluoro-2,6-dinitro-N,N-dipropyl-p-toluidine; 1,1'-dimethyl- 4,4'-bipyridinium ion; 2-chloro-2',6'-diethyl-(methoxymethyl) acetanilide; and 2-[1-(ethoxyimino)-butyl]-5-[(2-ethylthio) propyl]-3-hydroxy-2-cyclohexen-1-one (Poast ®).

The rates of application for compounds of the invention are determined by a number of factors including the active ingredient being applied, the particular action desired (e.g., general or selective control), the plant species to be modified and the stage of growth thereof, the part of the plant to be contacted with the toxic active ingredient, the formulation selected, weather and climate, etc. Thus, it is to be understood that all of the active ingredients of the present invention and compositions containing the same may not be equally effective at similar concentrations or against the same plant species. In non-selective preemergence and foliar treatments, the active ingredients of the invention are usually applied at an approximate rate of from about 0.1 to about 10 pounds/acre. In pre- and postemergence operations for selective uses, a dosage of about 0.01 to about 10 pounds/acre is generally applicable, a rate of 0.01 to 4 pounds/acre being preferred.

We claim:

1. A compound having the formula:

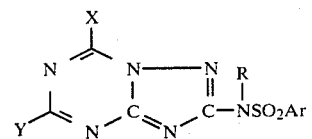

wherein Ar represents

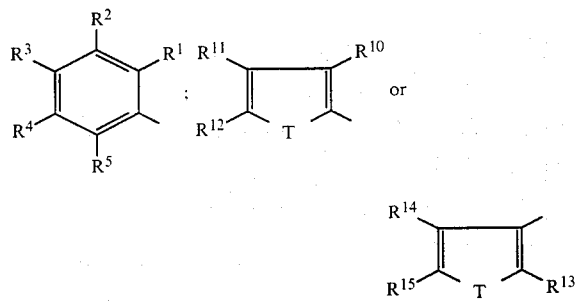

wherein R represents hydrogen, alkyl, alkenyl, alkynyl, phenylalkyl, substituted phenylalkyl, acyl, alkoxycarbonyl, phenoxycarbonyl, dialkylaminocarbonyl, alkylsulfonyl, phenylsulfonyl, alkylthiocarbonyl or phenylthiocarbonyl, each containing no more than 10 carbon atoms; $R^1$ represents halo, $-NO_2$, phenyl, $-CF_3$, $W-OCF_3$, $-OCF_2CF_2H$, $-OCF_2CCl_2H$, $-OCH_2CF_3$, $-SCF_3$, $-SCF_2CF_2H$, $-SCF_2CCl_2H$, $-SOCF_3$, $-SOCF_2CF_2H$, $-SOCF_2CCl_2H$, $-SO_2CF_3$, $-SO_2CF_2CF_2H$, $-SO_2CF_2CCl_2H$, $-SR^6$, $-SOR^6$, $-SO_2R^6$, $-CN$, $-COOR^7$, $-CONR^8(R^9)$, $-SO_2NR^8R^9$, $-SO_3R^8$ and $-SO_3CH_2CF_3$; $R^2$ and $R^4$ represent H, halo, $C_1-C_4$ alkyl and $-OR^8$; $R_3$ is H; and $R^5$ represents H, $C_1-C_4$ alkyl, $C_1-C_4$ alkoxy, halo, $NO_2$, $CF_3$, $-OCF_3$, $-OCF_2$ $Cf_2H$, $-OCF_2CCl_2H$, $-OCH_2CF_3$, $-SCF_3$, $-SCF_2CF_2H$, $-SCF_2CCl_2H$, $-SOCF_3$, $-SOCF_2CF_2H$, $-SOCF_2CCl_2H$, $-SO_2CF_3$, $-SO_2CF_2CF_2H$, $-SO_2CF_2CCl_2H$, $-SR^6$, $-SOR^6$, $-SO_2R^6$, $-CN$, $COOR^7$, $-CONR^8(R^9)$, $-SO_3R^8$, and $-SO_3CH_2CF_3$ wherein $R^6$ represents phenyl or $C_1-C_4$ alkyl, $R^7$ represents $C_1-C_6$ alkyl, alkenyl or alkynyl and $R^8$ and $R^9$ individually represent $C_1-C_4$ *alkyl; and X and Y independently represent H halogen*, $C_1-C_4$ alkyl, $C_1-C_4$ alkoxy, $C_1-C_4$ haloalkyl, $C_1-C_4$ haloalkoxy, or $C_1-C_4$ alkylthio groups; T represent O or S; $R^{10}$, $R^{11}$ and $R^{12}$ independently represent hydrogen, $C_1-C_4$ alkyl or halo; and $R^{13}$, $R^{14}$ and $R^{15}$ independently represent hydrogen, $C_1-C_4$ alkyl, halo or $COOR^{16}$ wherein $R^{16}$ represents $C_1-C_6$ alkyl, alkenyl or alkynyl.

2. Compound of claim 1 wherein X and Y independently represent hydrogen, $C_1-C_4$ alkyl, $C_1-C_4$ alkoxy or $C_1-C_4$ alkylthio groups.

3. Compound of claim 1 wherein X and Y are methyl.

4. A composition comprising an inert carrier in admixture with a herbicidally effective amount of a compound having the formula:

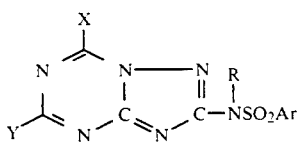

wherein Ar represents

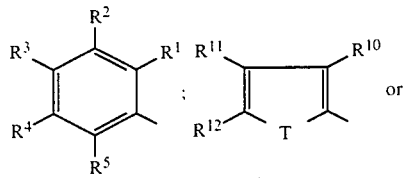

wherein R represents hydrogen, alkyl, alkenyl, alkynl, phenylalkyl, substituted phenylalkyl, acyl, alkoxcarbonyl, phenoxycarbonyl, dialkylaminocarbonyl, alkylsulfonyl, phenylsulfonyl, alkylthiocarbonyl or phenylthiocarbonyl, each containing no more than 10 carbon atoms; $R^1$ represents halo, —$NO_2$, phenyl, —$CF_3$, —$OCF_3$, —$OCF_2CF_2H$, —$OCF_2CCl_2H$, —$OCH_2CF_3$, —$SCF_3$, —$SCF_2CF_2H$, —$SCF_2CCl_2H$, —$SOCF_3$, —$SOCF_2CF_2H$, —$SOCF_2CCl_2H$, —$SO_2CF_3$, —$SO_2CF_2H$, —$SO_2CF_2CCL_2H$, —$SR^6$, —$SOR^6$, —$SO_2R^6$, —CN, —$COOR^7$—$CONR^8(R^9)$, —$SO_2NR^8R^9$, —$SO_3R^8$ and —$SO_3CH_2CF_3$; $R^2$ and $R^4$ represent H, halo, $C_1$-$C_4$ alkyl and —$OR^8$; $R^3$ is H ; and $R^5$ represents H, $C_1$-$C_4$ alkyl, $C_1$-$C_4$ alkoxy, halo, $NO_2$, $CF_3$, —$OCF_3$, —$OCF_2CF_2H$, —$OCF_2CCl_2H$, —$OCH_2CF_3$, —$SCF_2CF_2H$, —$SCF_2CCl_2H$, —$SOCF_3$, —$SOCF_2CF_2H$, —$SOCF_2CCl_2H$, —$SO_2CF_3$, —$SO_2CF_2H$, —$SO_2CF_2CCl_2H$, —$SR^6$, —$SOR^6$,—$SO_2R^6$, —CN, —$COOR^7$, —$CONR^8(R^9)$, —$SO_3R^8$, and —$SO_3CH_2CF_3$ wherein $R^6$ represents phenyl or $C_1$-$C_4$ alkyl, $R^7$ represents $C_1$-$C_6$ alkyl, alkenyl or alkynyl; and $R^8$ and $R^9$ individually represent $C_1$-$C_4$ alkyl and X and Y X and independently represent H, halogen, $C_1$-$C_4$ alkyl, $C_1C_4$ alkoxy, $C_1$-$C_4$ haloalkyl, $C_1$-$C_4$ haloalkoxy, or $C_1$-$C_4$ alkylthio groups; T represents O of S; $R^{10}$, $R^{11}$ and $R^{12}$ independently represent hydrogen, $C_1$-$C_4$ alkyl or halo; and $R^{13}$, $R^{14}$ and $R^{15}$ indenpendently represent hydrogen, $C_1$-$C_4$ alkyl, halo or $COOR^{16}$ wherein $R^{16}$ represents $C_1$-$C_6$ alkyl, alkenyl or alkynyl.

5. Composition of claim 4 wherein X and Y independently represent hydrogen, $C_1$-$C_4$ alkyl, $C_1$-$C_4$ alkoxy, or $C_1$-$C_4$ alkylthio groups.

6. Composition of claim 4 wherein X and Y are methyl.

7. Method of controlling undesired vegetation which comprises the application of a herbicidally effective amount of a compound having the formula:

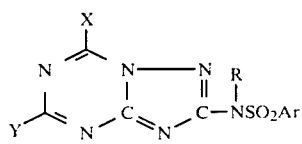

wherein Ar represents

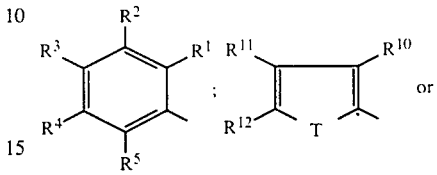

wherein R represents hydrogen, alkyl, alkenyl, alkynyl, phenylalkyl, substituted phenylalkyl, acyl, alkoxycarbonyl, phenoxycarbonyl, dialkylaminocarbonyl, alkylsulfonyl, phenylsulfonyl, alkylthiocarbonyl or phenylthiocarbonyl, each containing no more than 10 carbon atoms; $R^1$ represents halo, —$NO_2$, phenyl, —$CF_3$, —$OCF_3$, —$OCF_2CF_2H$, —$OCF_2CCl_2H$, —$OCH_2CF_3$, —$SCF_3$, —$SCF_2CF_2H$, —$SCF_2CCl_2H$, —$SOCF_3$, —$SOCF_2CF_2H$, —$SOCF_2CCl_2H$, —$SO_2CF_3$, —$SO_2CF_2CF_2H$, —$SO_2CF_2CCL_2H$, —$SR^6$, —$SOR^6$, —$SO_2R^6$, —CN, —$COOR^7$, —$CONR^8(R^9)$, —$SO_2NR^8R^9$, —$SO_3R^8$ and —$SO_3CH_2CF_3$; $R^2$ and $R^4$ represent H, halo, $C_1$-$C_4$ alkyl and —$OR^8$; $R^3$ is H; and $R^5$ represents H, $C_1$-$C_4$ alkyl, $C_1$-$C_4$ alkoxy, halo, $NO_2$, $CF_3$, —$OCF_3$, —$OCF_2CF_2H$, —$OCF_2CCl_2H$, —$OCH_2CF_3$, —$SCF_3$, —$SCF_2CF_2H$, $SCF_2CCl_2H$, —$SOCF_3$, —$SOCF_2CF_2H$, —$SOCF_2CCl_2H$, —$SO_2CF$hd 3, —$SO_2CF_2CF_2H$, —$SO_2CF_2CCl_2H$, —$SR^6$, —$SOR^6$, —$SO_2R^6$, —CN, —$COOR^7$, —CN, —$COOR^7$, —$CONR^8(R^9)$, —$SO_3R^8$, and —$SO_3CH_2CF_3$ wherein $R_6$ represents phenyl or $C_1$-$C_4$ alkyl, $R^7$ represents $C_1$-$C_6$ alkyl, alkenyl or alkynyl and $R^8$ and $R^9$ individually represent $C_1$-$C_4$ alkyl; and X and Y independently represent H, halogen, $C_1$-$C_4$ alkyl, $C_1$-$C_4$ alkoxy, $C_1$-$C_4$ haloalkyl, $C_1$-$C_4$ haloalkoxy, or $C_1$-$C_4$alkylthio groups; T represents O or S; $R^{10}$, $R^{11}$ and $R^{12}$ independently represent hydrogen, $C_1$-$C_4$ alkyl or halo; and $R^{13}$, $R^{14}$ and $R^{15}$ independently represent hydrogen, $C_1$-$C_4$ alkyl, halo or $COOR^{16}$ wherein $R^{16}$ represents $C_1$-$C_4$ alkyl, alkenyl or alkynyl.

8. Method of claim 7 wherein X and Y independently represent hydrogen, $C_1$-$C_4$ alkyl, $C_1$-$C_4$ alkoxy or $C_1$-$C_4$ alkylthio groups.

9. Method of claim 7 wherein X and Y are methyl.

10. Method of claim 7 wherein Ar is

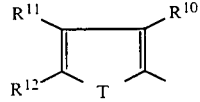

Wherein T represent O or S, and $R^{10}$, $R^{11}$ and $R^{12}$ independently represent hydrogen, $C_1$-$C_4$ alkyl and halo.

11. Method of claim 7 wherein Ar is

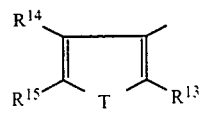

wherein T represent O or S, and $R^{13}$, $R^{14}$ and $R^{15}$ indeppendently represent hydrogen, $C_1$-$C_4$ alkyl, halo and $COOR^{16}$ wherein $R^{16}$ represents $C_1$-$C_6$ alkyl, alkenyl or alkynyl.

* * * * *

UNITED STATES PATENT AND TRADEMARK OFFICE
CERTIFICATE OF CORRECTION

PATENT NO. : 4,685,958                                        Page 1 of 3

DATED : August 11, 1987

INVENTOR(S) : Norman R. Pearson, William A. Kleschick

It is certified that error appears in the above-identified patent and that said Letters Patent is hereby corrected as shown below:

Column 2, line 37, "and phenyl" should read -- or phenyl --.
Column 2, line 50, "Wherein $R^1$" should read -- wherein $R^1$ --.
Column 7, line 53, "$K_2CO_3$in" should read -- $K_2CO_3$ in --.
Column 8, line 36, "C. IR and $^b$ $^1$H NMR" should read -- C. IR and $^1$H NMR --.
Column 11, line 6, "concentrations from about 0.05" should read -- Concentrations from about 0.05 --.
Column 12, line 41, "$CF_3$, W -" should read -- $CF_3$, - --.
Column 12, line 48, "$OR^8$; $R_3$" should read -- $OR^8$; $R^3$ --.
Column 12, line 50, "-$OCF_2$ $Cf_2H$," should read -- -$OCF_2CF_2H$, --.
Column 12, line 58, "represent H halogen," should read -- represent H, halogen --.
Column 12, line 60, "represent O" should read -- represents O --.
Column 13, line 29, "alkoxcarbo-" should read -- alkoxycarbo- --.
Column 13, line 37, "-$SO_2CF_2H$," should read -- -$SO_2CF_2CF_2H$, --.
Column 13, line 37, "-$SO_2CF_2CCL_2H$," should read -- -$SO_2CF_2CCl_2H$, --.
Column 13, line 44, "-$OCH_2CF_3$, $SCF_2CF_2H$," should read -- -$OCH_2CF_3$, -$SCF_3$, -$SCF_2CF_2H$, --.
Column 13, line 46, "-$SO_2CF_2$CFhd 2H," should read -- -$SO_2CF_2CF_2H$, --.

UNITED STATES PATENT AND TRADEMARK OFFICE
CERTIFICATE OF CORRECTION

PATENT NO. : 4,685,958

DATED : August 11, 1987

INVENTOR(S) : Norman R. Pearson, William A. Kleschick

It is certified that error appears in the above-identified patent and that said Letters Patent is hereby corrected as shown below:

Column 13, line 51, "$C_1-C_4$ alkyland X and Y X and" should read -- $C_1-C_4$ alkyl; and X and Y --.

Column 13, line 52, "$C_1C_4$ alkoxy," should read -- $C_1-C_4$ alkoxy, --.

Column 13, line 55, "sents O of S;" should read -- sents O or S; --.

Column 13, line 57, "indenpendently" should read -- independently --.

Column 14, line 25, "kysulfonyl," should read -- kylsulfonyl, --.

Column 14, line 29, "$-SO_2CF_2CCL_2H$," should read -- $-SO_2CF_2CCl_2H$, --.

Column 14, line 34, "$-SCF_2CF_2H$, $SCF_2CCl_2H$," should read -- $-SCF_2CF_2H$, $-SCF_2CCl_2H$, --.

Column 14, line 36, "$-SO_2CFhd\ 3$," should read -- $-SO_2CF_3$, --.

Column 14, line 37, "$-COOR^7$, $-CN$," should read -- $-COOR^7$, --.

Column 14, line 38, "$COOR^7$, $-CONR^8(R^9)$," should read -- $-CONR^8(R^9)$, --.

Column 14, line 39, "wherein R6 represents" should read -- wherein $R^6$ represents --.

Column 14, line 44, "$C_1-C_4$alkylthio" should read -- $C_1-C_4$ alkylthio --.

Column 14, line 48, "$C_1-C_4$ alkyl" should read -- $C_1-C_6$ alkyl --.

Column 14, line 56, "Wherein T represent O" should read -- wherein T represents O --.

UNITED STATES PATENT AND TRADEMARK OFFICE
CERTIFICATE OF CORRECTION

PATENT NO. : 4,685,958

DATED : August 11, 1987

INVENTOR(S) : Norman R. Pearson, William A. Kleschick

It is certified that error appears in the above-identified patent and that said Letters Patent is hereby corrected as shown below:

Column 14, line 65, "wherein T represent O" should read -- wherein T represents O --.

Signed and Sealed this

Twenty-fourth Day of May, 1988

Attest:

DONALD J. QUIGG

*Attesting Officer*      *Commissioner of Patents and Trademarks*